United States Patent [19]

Lemoine et al.

[11] Patent Number: 5,162,208
[45] Date of Patent: Nov. 10, 1992

[54] *SACCHAROMYCES CEREVISIAE* STRAIN PRODUCTIVE OF A HETEROLOGOUS PROTEIN AND PROCESS FOR PREPARING THE SAID HETEROLOGOUS PROTEIN BY FERMENTATION OF THE SAID STRAIN

[75] Inventors: Yves Lemoine, Strasbourg; Martine Nguyen, Wittersheim, both of France; Tilman Achstetter, Oberkirch, Fed. Rep. of Germany

[73] Assignee: Transgene S.A., Courbevoie, France

[21] Appl. No.: 500,884

[22] Filed: Mar. 29, 1990

[30] Foreign Application Priority Data

Mar. 31, 1989 [FR] France ................. 89 04306

[51] Int. Cl.[5] .......................... C12N 1/19; C12P 21/00
[52] U.S. Cl. ................................ 435/69.1; 435/69.2; 435/255; 435/320.1; 435/172.3
[58] Field of Search ............ 435/69.1, 255, 172.3

[56] References Cited

FOREIGN PATENT DOCUMENTS 252854 1/1988 European Pat. Off. .

OTHER PUBLICATIONS

Wolf et al. Eur J Biochem 73:553 (1977) abstract only.
Zubenko et al. Genetics 102:679 (1982).
Valls et al. Cell 48:887 (1987).
Ma et al. Gene 58:201 (1987).
Struhl et al. PNAS 6:1035 (1979).
Lee et al. Biochem Biophy Res Comm 85:1135 (1978).

*Primary Examiner*—Richard A. Schwartz
*Assistant Examiner*—John Le Guyader
*Attorney, Agent, or Firm*—Cushman, Darby & Cushman

[57] ABSTRACT

The invention relates to a new strain of *Saccharomyces cerevisiae* productive of a heterologous protein, and more especially of hirudin, characterized by a suppression of the proteolytic function encoded by the PRC1 gene. More specifically, this deficiency is due to a mutation or more especially to a deletion of the PRC1 structural gene.

8 Claims, 5 Drawing Sheets

FIG.1

| | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 HV1 | VAL | VAL | TYR | THR | ASP | CYS | THR | GLU | SER | GLY | GLN | ASN | LEU | CYS | LEU |
| 2 HV2 | ILE | THR | TYR | THR | ASP | CYS | THR | GLU | SER | GLY | GLN | ASN | LEU | CYS | LEU |
| 3 HV3 | ILE | THR | TYR | THR | ASP | CYS | THR | GLU | SER | GLY | GLN | ASN | LEU | CYS | LEU |

| 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|
| CYS | GLU | GLY | SER | ASN | VAL | CYS | GLY | GLN | GLY | ASN | LYS | CYS | ILE | LEU |
| CYS | GLU | GLY | SER | ASN | VAL | CYS | GLY | LYS | GLY | ASN | LYS | CYS | ILE | LEU |
| CYS | GLU | GLY | SER | ASN | VAL | CYS | GLY | LYS | GLY | ASN | LYS | CYS | ILE | LEU |

| 31 | 32 | 33 | 34 | 35 | 36 | 37 | 38 | 39 | 40 | 41 | 42 | 43 | 44 | 45 | 46 | 47 |
|---|---|---|---|---|---|---|---|---|---|---|---|---|---|---|---|---|
| GLY | SER | ASP | GLY | GLU | LYS | ASN | GLN | CYS | VAL | THR | GLY | GLU | GLY | THR | PRO | LYS |
| GLY | SER | ASN | GLY | LYS | GLY | ASN | GLN | CYS | VAL | THR | GLY | GLU | GLY | THR | PRO | ASN |
| GLY | SER | GLN | GLY | LYS | ASP | ASN | GLN | CYS | VAL | THR | GLY | GLU | GLY | THR | PRO | LYS |

| 48 | 49 | 50 | 51 | 52 | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|
| PRO | GLN | SER | HIS | ASN | ASP | GLY | ASP | PHE | GLU | GLU | ILE | PRO | GLU | GLU | TYR | LEU | GLN |
| PRO | GLU | SER | HIS | ASN | ASN | GLY | ASP | PHE | GLU | GLU | ILE | PRO | GLU | GLU | TYR | LEU | GLN |
| PRO | GLN | SER | HIS | ASN | GLN | GLY | ASP | PHE | GLU | PRO | ILE | PRO | GLU | ASP | TYR | ASP | GLU |

↓ 64 65 66
ALA 63

1. From DODT et al. FEBS LETTERS 1984 165, 180-183.
2. From HARVEY et al. Proc. Natl. Acad. USA 1986 83, 1084-1088
3. From DODT et al. Biol. Chem. Hoppe-Seyler 1986 367, 803-811.

FIG_3

FIG_4

SACCHAROMYCES CEREVISIAE STRAIN PRODUCTIVE OF A HETEROLOGOUS PROTEIN AND PROCESS FOR PREPARING THE SAID HETEROLOGOUS PROTEIN BY FERMENTATION OF THE SAID STRAIN

The present invention relates to the preparation of heterologous proteins, and more especially of hirudin, by means of recombinant strains of S. cervisiae yeasts. Heterologous protein is understood to mean a protein which is neither produced naturally by the yeast nor necessary to its growth.

Yeasts are unicellular eukaryotic organisms; the yeast genus Saccharomyces comprises strains whose biochemistry and genetics are intensively studied in the laboratory; it also comprises strains used in the food industry (bread, alcoholic drinks, etc.) and consequently produced in very large quantities. The ease with which the genetics of Saccharomyces cerevisiae cells may be manipulated and the long industrial history of this species hence make it a host of choice for the production of foreign proteins using recombinant DNA techniques.

During the preparation of proteins by means of recombinant yeasts, it is often possible to observe that the protein produced from the yeast strain is not completely homogeneous, thereby leading to yields which are often insufficient for proteins of industrial importance intended for production in large quantities.

The Applicant has already concerned himself especially with the production of hirudin by recombinant strains of S. cerevisiae, described in European Patent Publications EP-A-0,252,854 and EP-A-0,273,800.

Hirudin, the main source of which is in the salivary glands of medicinal leeches in the form of a mixture of peptides of 65 and 66 amino acids, is a very specific and very effective inhibitor of thrombin. It is hence a very advantageous therapeutic agent, whose use in clinical medicine demands very high purity of the product and which is hence an attractive candidate for production by genetic engineering.

A number of natural variants of hirudin have been identified and designated HV1, HV2 and HV3. Their structure is depicted in FIG. 1 Subsequently, these natural variants, as well as other analogues, have been prepared by genetic engineering, especially by fermentation of S. cerevisiae strains, as described, for example, in European Patent Publications already cited, EP-A-0,252,854 and EP-A-0,273,800, in the name of the Applicant.

The Applicant has observed that the hirudin produced from the yeast strain described in European Patent Publication EP-A-0,252,854 is not entirely homogeneous. In particular, the major and correct form, which comprises 65 amino acids, is contaminated by two forms which elute from an HPLC column very close to the major peak and which correspond to cleavage products which have lost one or two amino acids at the C-terminal end. The presence of these two forms having 63 and 64 amino acids makes purification of the correct 65-amino acid form difficult.

For this reason, the invention aims to provide new means for obtaining a larger quantity of hirudin, corresponding to the correct, uncleaved form, from a strain of S. cerevisiae.

In the description below, the term "hirudin" will be employed to denote all natural hirudin variants or analogues which have undergone one or more mutations or deletions while retaining their antithrombotic activity In effect, the invention can relate to the production of all hirudins, although the examples below will relate more especially to the analogue designated rHV2Lys47 (that is to say a recombinant HV2 variant which has undergone a mutation of the amino acid Asp at position 47 to the amino acid Lys). The invention can also relate to all heterologous proteins produced by recombinant strains of S. cerevisiae for which the problem of lack of homogeneity due to the presence of cleaved forms, mentioned above, is encountered.

The subject of the invention is hence a recombinant strain of S. cerevisiae productive of a heterologous protein, transformed by an expression vector containing a DNA sequence coding for the heterologous protein, characterized in that it contains a suppression of the proteolytic function encoded by the PRC1 gene.

S. cerevisiae strains have a number of proteolytic functions which are expressed, in the yeast cell, in different places It appears that the vacuolar proteases play a special part in the lack of homogeneity of the heterologous proteins, and especially of hirudin, produced by S. cerevisiae strains.

The invention is hence based on a demonstration of the precise part played by the proteolytic function encoded by the PRC1 gene, and corresponding to a vacuolar endogenous protease of yeast, carboxypeptidase yscY, in the lack of homogeneity of the hirudin The suppression of the proteolytic function encoded by the PRC1 gene may be accomplished in different ways. For example, one or more mutations in the corresponding structural gene, and in particular a partial or total deletion of the gene, may be mentioned. To avoid any reversion of the mutation, it can be advantageous to proceed by way of deletion.

All strains of S. cerevisiae industrially usable for the production of heterologous proteins can form the subject of the invention, inasmuch as they have the stated deficiency.

Generally speaking, the strains used can be haploid strains of S. cerevisiae which carry the HO mutation, conferring heterothallism, which are of the alpha mating type and which have mutations affecting the URA3 gene as well as different genes of amino acid biosynthesis. The advantage of using heterothallic strains is to enable the strain to be preserved in a haploid and nonsporulating form. In effect, when the MFalpha1 promoter of yeast is used for the synthesis of hirudin, it was found that this promoter functioned optimally in non-sporulating strains of the alpha mating type. In HO wild-type yeasts, the haplophase is a transitory state which disappears after one or two divisions. The laboratory yeasts are ho mutants in which the haplophase is stable.

Naturally, promoters other than that of the alpha pheromone may be used, which do not necessarily require heterothallic strains. There may be mentioned, for example, yeast promoters whose functionality has been confirmed by the transcription of genes coding for heterologous proteins: the PGK, PH05, GAL1 promoter, and the like.

The use of ura3 mutants permits transformation of the strains by a vector suited to the expression of hirudin, as well as the selection of transformed cells productive of hirudin by the composition of the culture medium, which must be devoid of pyrimidine (essentially uracil, cytosine and uridine).

Strains which have a pep4-3 genotype (gene referred to as PRA1 or PEP4) may be mentioned more especially. The protease yscA is also vacuolar in its localization and is synthesized in the form of an inactive precursor. The precursor may be activated by cleavage, either spontaneously, or enzymatically by means of the protease yscA itself. Through its proteolytic activity, the protease yscA is involved in the activation of a number of vacuolar proteins, thereby generating proteases, RNases, and the like. Inactivation of the protease yscA by genetic mutation results in an accumulation of all these inactive zymogens at the expense of the active forms. Thus, the pep4-3 mutant shows a decrease in several enzyme activities in the vacuole, thereby contributing to the effect desired according to the invention.

Finally, the invention also relates to a process for preparing hirudin by fermentation of a recombinant strain of S. cerevisiae, according to which an S. cerevisiae strain according to the invention is cultured in a suitable medium and the hirudin obtained is recovered.

Other features and advantages of the invention will become apparent during the detailed description which follows, which illustrates the invention by means of examples of production of the hirudin variant rHV2Lys47 by an S. cerevisiae strain according to the invention, accompanied by the following FIGS. 1 to 5:

FIG. 1 shows the sequences of the hirudin variants HV1, HV2 and HV3.

The genotypic and phenotypic characteristics of the reference strains and the background details of their construction are specified below:

1. Reference strain TGY1sp4

Genotype : MATalpha, ura3-251,-328,-273, his3-11,-15 (the URA3 gene which is defective corresponds to the enzyme OMP decarboxylase; this defect is corrected in the presence of a plasmid carrying the ura3 gene. This complementation constitutes the selection system for the hirudin expression vector, it being possible for the strain carrying the plasmid to multiply in minimum medium +casamino acids, without uracil).

Phenotype ura- his-; alpha mating sign

Background details of the strain:

The strain TGY1sp4 is the result of crossing two collection strains FL ura3 MATa × GRF18 MATalpha.

The strain aFL ura3 was selected by F. Lacroute (University of Strasbourg) as a mutant requiring uracil for growth; it is isogenic with the strain FL100 (ATCC strain 28383), from which it is derived and from which it differs only by the ura- character; this character is due to three mutations: ura3-251,-328,-373.

The strain alphaGRF 18 was selected by G. Fink (USA) and is used in many laboratories. Its use in genetic manipulations by transformation is described, for example, by M. Rudolph, I. Koenig-Rauseo and A. Hinnen (Gene 36, 1985, 87-95).

The genotype of the strain GRF 18 is: MATalpha, his3-11, -15, leu2-3,-112.

2. Reference strain TGY20.3

Genotype: MATalpha, ura3-251,-373,-328, his3-11,-15, leu2-3,-112, pep4-3.

Phenotype: ura-, his-, leu-, crosses with strains of the MATalpha type: does not sporulate; shows a large decrease in proteinase yscA and yscB and carboxypeptidase yscY activities.

The background details of the strain are shown diagrammatically below:

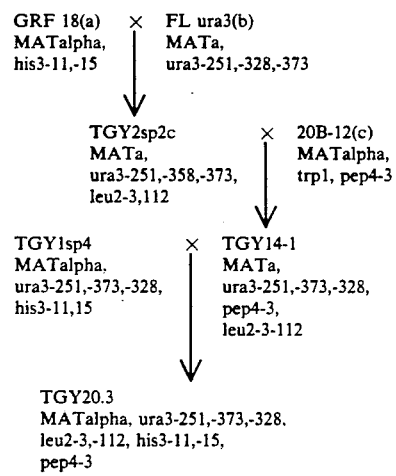

a) strain selected by G. Fink (see above)
b) strain selected by F. Lacroute, isogenic with the strain FL100 (see above)
c) strain obtained from the "Yeast Genetic Stock Center" (Berkeley, Calif. 94720) as described by E. W. Jones (1977, Genetics 95, 23).

EXAMPLE 1

Construction of strains containing the PRC1 gene, partially deleted

A. Cloning of the PRC1 gene

The sequence of the PRC1 gene has been published by Valls, L. A. et al. [Cell, 48 p 887–897 (1987)]. Two oligonucleotides are constructed from this sequence. The first is complementary to the 5' region of the gene and its sequence is as follows:

5' AAG AAA GAC TGG GAC TTT GTG 3'

The second is complementary to the 3' region of the gene and its sequence is as follows:

5' GAT TGG ATG AAG CCT TAC CAC 3'

An E. coli clone containing the PRC1 gene inserted into pFL1 is selected from a yeast genomic library (fragments of chromosomal DNA partially digested with Sau3A, which are inserted into the BamHI site of pFL1 [Parent, S. A. et al. Yeast 1 83–138 (1985)] and by hybridization with these two oligonucleotides.

Figure 2:
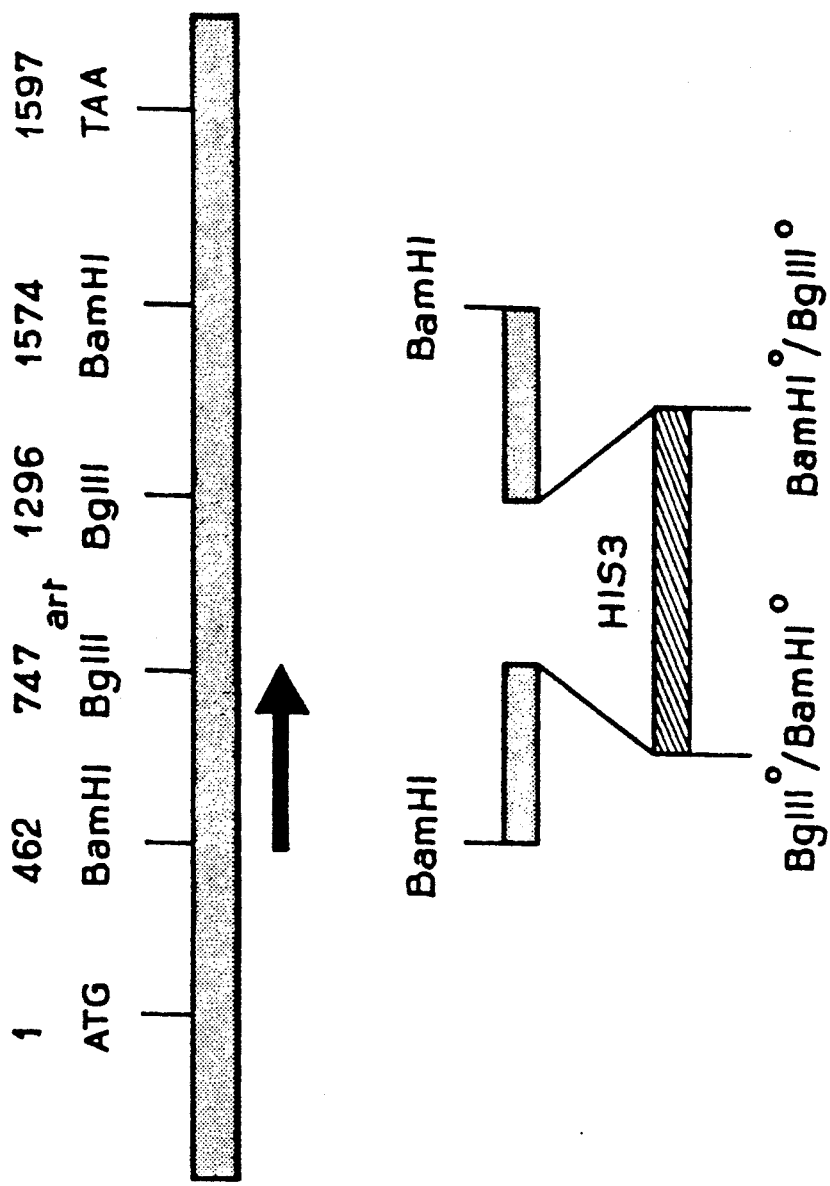
FIG. 2 is a diagrammatic representation of the restriction map of the PRC1 gene in its chromosomal form and of the fragment containing the inserted HIS3 gene.

B. Creation of the partial deletion in the PRC1 gene (FIG. 2)

In the PRC1 gene, a BglII site is found in the coding sequence. By directed mutagenesis, the second BglII site is introduced upstream of the natural BglII site 549 base pairs from the latter, that is to say still in the coding sequence. This mutagenesis is carried out using the following oligonucleotide:

5' CGATGTGGAGATCTTGGCC 3'

This BglII fragment is then excised and replaced by a 1.2-kb BamHI fragment containing the sequence of the HIS3 gene of the yeast [Struhl K. (1985) Nucl. Acids Res. 13 8587-8601], and obtained after isolation and cloning into M13mp8. The active site of the product of the PRC1 gene is thereby removed.

C. Selection of strains containing the mutated gene prc1-d::HIS3 described in B

*S. cerevisiae* strains TGY1sp4 (MATalpha, his3, ura3) and TGY20.3 (MATalpha, his3, ura3, leu2, pep4-3) are transformed with an approximately 1.7-kb BamHI fragment, enabling the mutated allele prc1-d::HIS3 to be generated by chromosomal exchange. Clones prototrophic with respect to histidine are selected, and four transformants of each strain are then analyzed for stability of the HIS+ character. Finally, the chromosomal DNA of these transformants is analyzed by Southern hydridization in order to check that the wild-type PRC1 allele has indeed been exchanged with the mutated allele prc1-d::HIS3. Two strains TGY1sp4 prc1-d::HIS3 and TGY20.3 prc1-d::HIS3 are thereby obtained.

EXAMPLE 2

Construction of plasmid pTG2958

Figure 3:
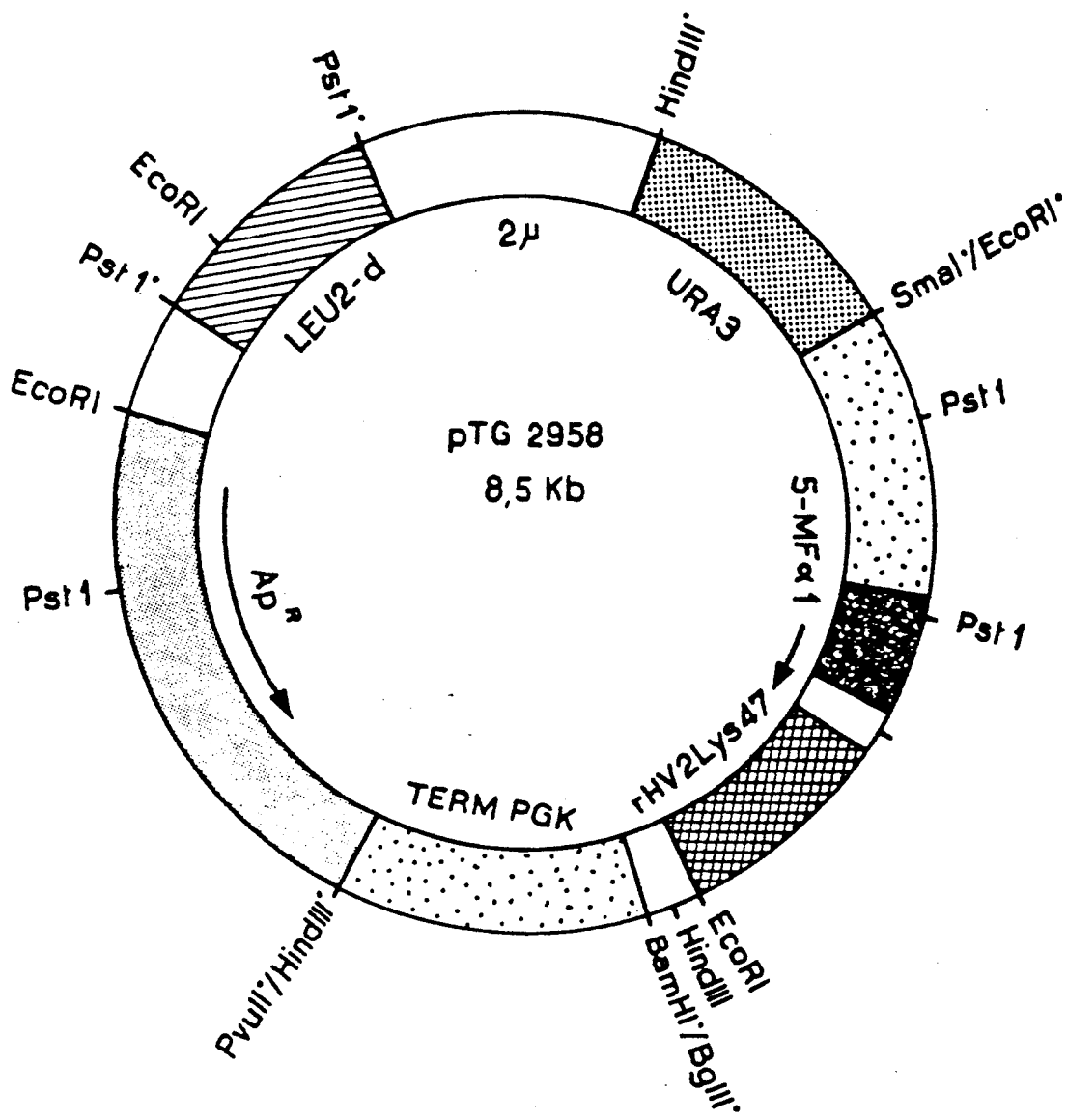
FIG. 3 shows the structure of plasmid pTG2958.

Plasmid pTG2958 (FIG. 3) differs little from plasmid pTG1833 described in European Patent Publication EP-A-252,854, carrying the coding sequence for rHV2Asp47. Plasmid pTG2958 does not contain the artificially introduced HindIII restriction site. Plasmid pTG2958 contains:

- a fragment of 547 base pairs corresponding to the 5' region of the MFalpha1 gene (containing the promoter, the sequence coding for the signal peptide, the "pro" region and a sequence coding for the peptide Lys-Arg),
- a fragment of 234 base pairs containing the complementary DNA for rHV2Lys47,
- a fragment of 243 base pairs comprising the PGK terminator of yeast,
- the PvuII-EcoRI fragment of pBR322 comprising, inter alia, the origin of replication of this plasmid and the gene for resistance to ampicillin (2292 base pairs),
- the EcoRI-HindIII fragment of the 2μ plasmid of yeast (B form), containing the LEU2 gene of yeast, in deleted form and inserted into the PstI site,
- a HindIII-SmaI fragment of the URA3 gene of yeast.

EXAMPLE 3

Figure 4:
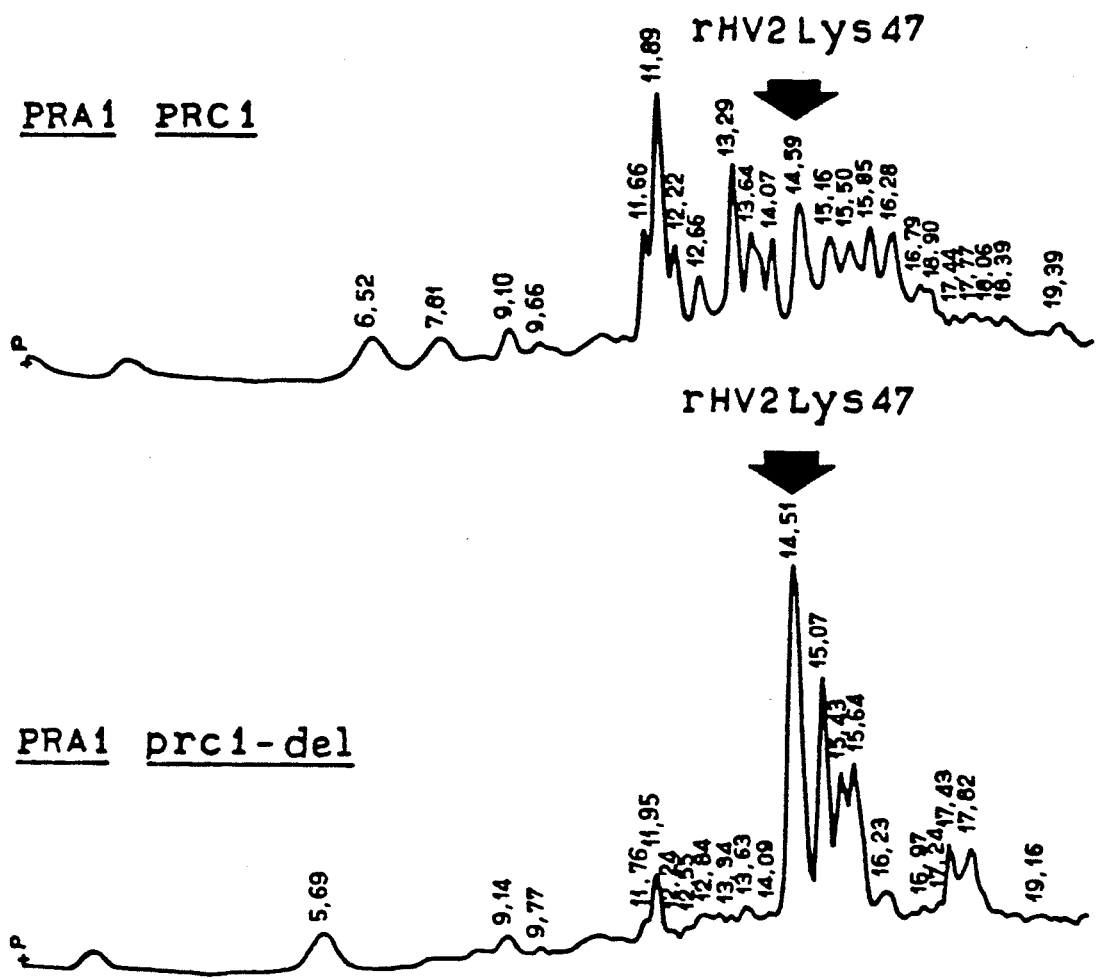
FIG. 4 shows the HPLC profile obtained from culture supernatants of the strains TGY1sp4 and TGY1sp4 prc1-d::HIS3 transformed by plasmid pTG2958.
Figure 5:
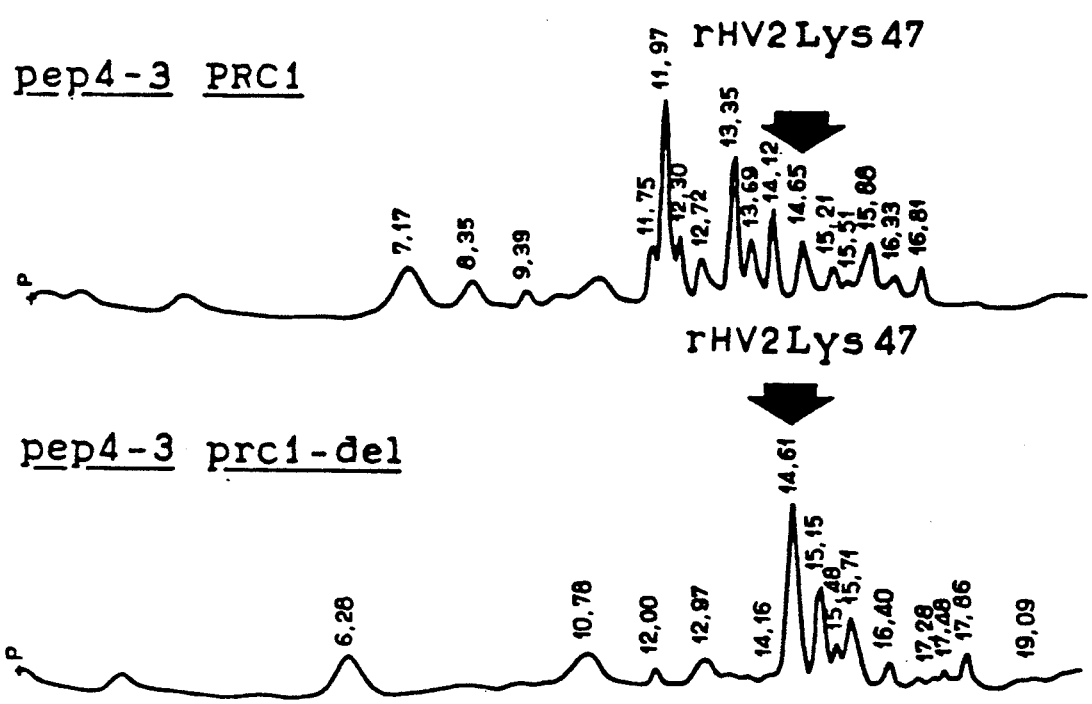
FIG. 5 shows the HPLC profile obtained from culture supernatants of the strains TGY20.3 and TGY20.3 prc1-d::HIS3 transformed by plasmid pTG2958.

Production of rHV2Lys47 by the strains obtained above containing the PRC1 gene in a deleted form The yeast strains are transformed with plasmid pTG2958 by the lithium acetate method [Ito, H. et al. J. Bacteriol. 1983], and the clones prototrophic with respect to uracil are selected They are then cultured in an Erlenmeyer at 30° C. on a selective medium (0.7% of nitrogenous bases for yeasts (Yeast Nitrogen Base), 0.5% of casamino acids and 1% of glucose). After 48 hours of culture, cells and supernatants are separated by centrifugation and the quantity of rHV2Lys47 is determined in the supernatant by separation on an HPLC column (Nucleosil C8 3 μm SFCC N333 column equipped with a Nucleosil C8 5 μm PSF35-1 cartridge precolumn) and integration of the peak corresponding to the 65-amino acid form (FIGS. 4 and 5). The results of these assays are presented in Table 1 (the quantities are given in μg of rHV2Lys47 per optical density unit (A600) of the cells obtained after harvesting on a stationary phase).

TABLE 1

| Strain | Significant genotype | Production of rHV2Lys47 in μg/A600 |
| --- | --- | --- |
| TGY1SP4 | PRA1 PRC1 | 0.055 |
| — | PRA1 prc1-del::HIS3 | 0.255 |
| TGY20.3 | pep4-3 PRC1 | 0.024 |
| — | pep4-3 prc1-del::HIS3 | 0.072 |

The assays of rHV2Lys47 clearly demonstrate an increase in the production of rHV2Lys47 by a factor of approximately four for the strains in which the PRC1 gene has been deleted according to the invention. Immunoassay using specific monoclonal antibodies directed towards the C-terminal portion (permitting discrimination between the degraded forms and the correct form) confirms these results.

The strain TGY1sp4 prc1-d::HIS3 transformed by plasmid pTG2958 was deposited on Mar. 31, 1989 with the C.N.C.M. (National Collection of Microorganism Cultures), rue du Dr. Roux 75724 PARIS under number I-854.

We claim:

1. A recombinant yeast strain that produces a heterologous protein, which is transformed by an expression vector comprising a first DNA fragment encoding said protein, and in which strain the proteolytic function naturally associated with protease yscY has been suppressed by mutating the PRC1 gene.

2. The recombinant yeast strain according to claim 1, wherein said expression vector further comprises a second DNA fragment encoding a signal peptide that promotes secretion of said protein.

3. The recombinant yeast strain according to claim 1, wherein the proteolytic function naturally associated with protease yscY is suppressed by partially deleting the PRC1 gene.

4. The recombinant yeast strain according to claim 1, wherein the proteolytic function naturally associated with yscY is suppressed by partially deleting, the region of the PRC1 gene encoding the mature form of yscY.

5. The recombinant yeast strain according to claim 1 wherein said strain produces hirudin.

6. The recombinant yeast strain according to claim 5 wherein said strain produces hirudin HV2Lys47.

7. The recombinant yeast strain according to claim 1 wherein said strain is a strain of *Saccharomyces cerevisiae*.

8. A process for preparing a protein heterologous to yeast, which comprises culturing the yeast strain according to claim 1 under conditions such that said protein is produced recovering said protein.

* * * * *